United States Patent [19]

Zones et al.

[11] Patent Number: 4,952,744

[45] Date of Patent: Aug. 28, 1990

[54] NEW ZEOLITE SSZ-23 AND ITS USE IN CONVERSION OF LOWER ALKANOLS INTO HYDROCARBONS

[75] Inventors: Stacey I. Zones, San Francisco; R. A. Innes, San Rafael, both of Calif.

[73] Assignee: Chevron Research Company, San Francisco, Calif.

[21] Appl. No.: 424,475

[22] Filed: Oct. 20, 1989

Related U.S. Application Data

[60] Division of Ser. No. 333,654, Apr. 5, 1989, Pat. No. 4,902,844, which is a continuation-in-part of Ser. No. 823,705, Jan. 29, 1986, abandoned.

[51] Int. Cl.$^5$ .............................................. C07C 1/20
[52] U.S. Cl. .................................................... 585/640

[58] Field of Search ................................ 585/640, 639

[56] References Cited

U.S. PATENT DOCUMENTS

| | | | |
|---|---|---|---|
| 4,300,013 | 11/1981 | Whittam | 585/481 |
| 4,400,572 | 8/1983 | Lake et al. | 585/481 |
| 4,902,844 | 2/1990 | Zones et al. | 585/481 |

*Primary Examiner*—Asok Pal
*Attorney, Agent, or Firm*—T. G. De Jonghe; V. J. Cavalieri; C. E. Rincon

[57] ABSTRACT

A crystalline zeolite SSZ-23 is prepared using an adamantane quaternary ammonium ion as a template. The zeolite is useful in converting lower alkanols to gasoline range hydrocarbons.

3 Claims, No Drawings

NEW ZEOLITE SSZ-23 AND ITS USE IN CONVERSION OF LOWER ALKANOLS INTO HYDROCARBONS

CROSS-REFERENCE TO RELATED APPLICATION

This is a division of application Ser. No. 333,654, filed 4-5-89, now U.S. Pat. No. 4,902,844, which is a C-I-P of Ser. No. 823,705, 1-29-86, abandoned.

BACKGROUND OF THE INVENTION

Natural and synthetic zeolitic crystalline aluminosilicates are useful as catalysts and adsorbents. These aluminosilicates have distinct crystal structures which are demonstrated by X-ray diffraction. The crystal structure defines cavities and pores which are characteristic of the different species. The adsorptive and catalytic properties of each crystalline aluminosilicate are determined in part by the dimensions of its pores and cavities. Thus, the utility of a particular zeolite in a particular application depends at least partly on its crystal structure.

Because of their unique molecular sieving characteristics, as well as their catalytic properties, crystalline aluminosilicates are especially useful in such applications as gas drying and separation and hydrocarbon conversion. Although many different crystalline aluminosilicates and silicates have been disclosed, there is a continuing need for new zeolites and silicates with desirable properties for gas separation and drying, hydrocarbon and chemical conversions, and other applications.

Crystalline aluminosilicates are usually prepared from aqueous reaction mixtures containing alkali or alkaline earth metal oxides, silica, and alumina. "Nitrogeous zeolites" have been prepared from reaction mixtures containing an organic templating agent, usually a nitrogen-containing organic cation. By varying the synthesis conditions and the composition of the reaction mixture, different zeolites can be formed using the same templating agent. Use of N,N,N-trimethyl cyclopentylammonium iodide in the preparation of Zeolite SSZ-15 molecular sieve is disclosed in my copending application Ser. No. 437,709, filed on Oct. 29, 1982; use of 1-azoniaspiro[4.4] nonyl bromide and N,N,N-trimethyl neopentylammonium iodide in the preparation of a molecular sieve termed "Losod" is disclosed in *Helv. Chim. Acta* (1974); Vol. 57, page 1533 (W. Sieber and W. M. Meier); use of quinuclidinium compounds to prepare a zeolite termed "NU-3" is disclosed in European Patent Publication No. 40016; use of 1,4-di(1-azoniabicyclo[2.2.2.]octane) lower alkyl compounds in the preparation of Zeolite SSZ-16 molecular sieve is disclosed in U.S. Pat. No. 4,508,837; use of N,N,N-trialkyl-1-adamantamine in the preparation of zeolite SSZ-13 molecular sieve is disclosed in U.S. Pat. No. 4,544,538.

SUMMARY OF THE INVENTION

I have prepared a family of crystalline aluminosilicate molecular sieves with unique properties, referred to herein as "Zeolite SSZ-23", or simply "SSZ-23", and have found a highly effective method for preparing SSZ-23.

SSZ-23 has a mole ratio of an oxide selected from silicon oxide, germanium oxide, and mixtures thereof to an oxide selected from aluminum oxide, gallium oxide, iron oxide, boron oxide and mixtures thereof greater than about 50:1 and having the X-ray diffraction lines of Table 1 below. The zeolite further has a composition, as synthesized and in the anhydrous state, in terms of mole ratios of oxides as follows: (0.1 to 3.0)$Q_2O$:(0.1 to 2.0)$M_2O$:$W_2O_3$:(greater than 50)$YO_2$ wherein M is an alkali metal cation, W is selected from aluminum, gallium, iron, boron and mixtures thereof, Y is selected from silicon, germanium and mixtures thereof, and Q is an adamantane quaternary ammonium ion. SSZ-23 zeolites can have a $YO_2$:$W_2O_3$ mole ratio greater than about 50:1. As prepared, the silica:alumina mole ratio is typically in the range of 70:1 to about 1500:1. Higher mole ratios can be obtained by treating the zeolite with chelating agents or acids to extract aluminum from the zeolite lattice. The silica:alumina mole ratio can also be increased by using silicon and carbon halides and other similar compounds. Preferably, SSZ-23 is an aluminosilicate wherein W is aluminum and Y is silicon.

My invention also involves a method for preparing SSZ-23 zeolites, comprising preparing an aqueous mixture containing sources of an adamantane quaternary ammonium ion, an oxide selected from aluminum oxide, gallium oxide, iron oxide, boron oxide and mixtures thereof, and an oxide selected from silicon oxide, germanium oxide, and mixtures thereof, and having a composition, in terms of mole ratios of oxides, falling within the following ranges: $YO_2/W_2O_3$, 50:1 to 1500:1; and $Q_2O/YO_2$ 0.05:1 to 0.80:1; wherein Y is selected from silicon, germanium, and mixtures thereof, W is selected from aluminum, gallium, iron, boron and mixtures thereof, and Q is an adamantane quaternary ammonium ion; maintaining the mixture at a temperature of at least 100° C. until the crystals of said zeolite are formed; and recovering said crystals.

DETAILED DESCRIPTION OF THE INVENTION

SSZ-23 zeolites, as synthesized, have a crystalline structure whose X-ray powder diffraction pattern shows the following characteristic lines:

TABLE 1

| 2 θ | d/n | $I/I_o$ |
|---|---|---|
| 8.15 | 10.85 | 100 |
| 8.58 | 10.31 | 45 |
| 9.50 | 9.31 | 55 |
| 10.55 | 8.39 | 40 |
| 17.60 | 5.04 | 45 |
| 18.54 | 4.79 | 80 |
| 19.65 | 4.52 | 65 |
| 20.06 | 4.43 | 65 |
| 21.53 | 4.13 | 100 |
| 22.16 | 4.011 | 50 |
| 22.72 | 3.914 | 70 |
| 24.87 | 3.580 | 45 |

Typical SSZ-23 aluminosilicate zeolites have the X-ray diffraction pattern of Tables 2-6 below.

The X-ray powder diffraction patterns were determined by standard techniques. The radiation was the K-alpha/doublet of copper and a scintillation counter spectrometer with a strip-chart pen recorder was used. The peak heights I and the positions, as a function of 2 θ where θ is the Bragg angle, were read from the spectrometer chart. From these measured values, the relative intensities, $100I/I_o$, where $I_o$ is the intensity of the strongest line or peak, and d, the interplanar spacing in Angstroms corresponding to the recorded lines, can be calculated. The X-ray diffraction pattern of Table 1 is characteristic of SSZ-23 zeolites. The zeolite produced by exchanging the metal or other cations present in the zeolite with various other cations yields substantially the same diffraction pattern although there can be minor shifts in interplanar spacing and minor variations in relative intensity. Minor variations in the diffraction pattern can also result from variations in the organic compound used in the preparation and from variations in the silica-to-alumina mole ratio from sample to sample. Calcination can also cause minor shifts in the X-ray diffraction pattern. Notwithstanding these minor perturbations, the basic crystal lattice structure remains unchanged.

After calcination the SSZ-23 zeolites have a crystalline structure whose X-ray powder diffraction pattern shows the following characteristic lines as indicated in Table 2 below.

TABLE 2

| 2θ | d/n | I/I$_o$ |
|---|---|---|
| 8.17 | 10.82 | 100 |
| 8.50 | 10.40 | 25 |
| 9.45 | 9.36 | 100 |
| 10.56 | 8.38 | 45 |
| 17.78 | 4.99 | 10 |
| 18.58 | 4.78 | 20 |
| 19.63 | 4.52 | 15 |
| 20.05 | 4.43 | 10 |
| 21.58 | 4.118 | 15 |
| 22.12 | 4.019 | 10 |
| 22.56 | 3.941 | 10 |
| 24.90 | 3.576 | 10 |

SSZ-23 zeolites can be suitably prepared from an aqueous solution containing sources of an alkali metal oxide, an adamantane quaternary ammonium ion, an oxide of aluminum, gallium, iron, boron or mixtures thereof, and an oxide of silicon or germanium, or mixture of the two. The reaction mixture should have a composition in terms of mole ratios falling within the following ranges:

| | Broad | Preferred |
|---|---|---|
| YO$_2$/W$_2$O$_3$ | 50–1500 | 70–1500 |
| OH$^-$/YO$_2$ | 0.125–0.90 | 0.20–0.50 |
| Q/YO$_2$ | 0.05–0.80 | 0.10–0.40 |
| M$^+$/YO$_2$ | 0.03–0.30 | 0.05–0.20 |
| H$_2$O/YO$_2$ | 20–300 | 40–80 |
| Q/Q+M$^+$ | 0.50–0.90 | 0.67–0.80 | wherein Q is an adamantane quaternary ammonium ion, Y is silicon, germanium or both, and W is aluminum, gallium, iron, boron or mixtures thereof. M is an alkali metal, preferably sodium or potassium. The organic adamantane compound which acts as a source of the adamantane quaternary ammonium ion employed can provide hydroxide ion.

When using the adamantane quaternary ammonium hydroxide compound as a template, it has also been found that purer forms of SSZ-23 are prepared when there is an excess of the adamantane quaternary ammonium hydroxide compound present relative to the amount of alkali metal hydroxide and that when the OH$^-$/SiO$_2$ molar ratio is greater than 0.40, then M$^+$/SiO$_2$ molar should be less than 0.20.

The adamantane quaternary ammonium ion component Q, of the crystallization mixture, is derived from an adamantane quaternary ammonium compound. Preferably, the adamantane quaternary ammonium ion is derived from a compound of the formula

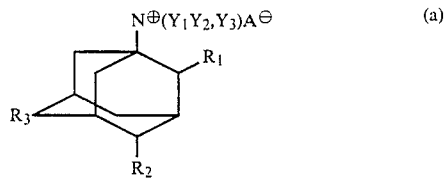

(a)

wherein each of Y$_1$ Y$_2$ and Y$_3$ independently is lower alkyl and most preferably methyl; A$^\ominus$ is an anion which is not detrimental to the formation of the zeolite; and each of R$_1$, R$_2$, and R$_3$ independently is hydrogen, or lower alkyl and most preferably hydrogen; and

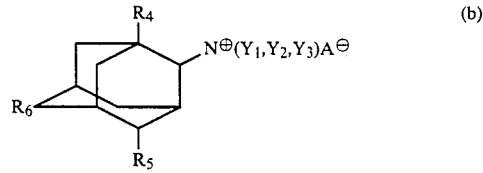

(b)

wherein each of R$_4$, R$_5$ and R$_6$ independently is hydrogen or lower alkyl; and most preferably hydrogen; each of Y$_1$, Y$_2$ and Y$_3$ independently is lower alkyl and most preferably methyl; and A$^\ominus$ is an anion which is not detrimental to the formation of the zeolite;

The adamantane quaternary ammonium compounds are prepared by methods known in the art.

By lower alkyl is meant alkyl of from about 1 to 5 carbon atoms.

A$^\ominus$ is an anion which is not detrimental to the formation of the zeolite. Representative of the anions include halogen, e.g., fluoride, chloride, bromide and iodide, hydroxide, acetate, sulfate, carboxylate, etc. Hydroxide is the most preferred anion. It may be beneficial to ion-exchange, for example, the halide for hydroxide ion, thereby reducing or eliminating the alkali metal hydroxide quantity required.

The reaction mixture is prepared using standard zeolitic preparation techniques. Typical sources of aluminum oxide for the reaction mixture include aluminates, alumina, and aluminum compounds such as AlCl$_3$ and Al$_2$(SO$_4$)$_3$. Typical sources of silicon oxide include silicates, silica hydrogel, silicic acid, colloidal silica, tetraalkyl orthosilicates, and silica hydroxides. Gallium, iron, boron and germanium can be added in forms corresponding to their aluminum and silicon counterparts. Salts, particularly alkali metal halides such as sodium chloride, can be added to or formed in the reaction mixture. They are disclosed in the literature as aiding the crystallization of zeolites while preventing silica occlusion in the lattice.

The reaction mixture is maintained at an elevated temperature until the crystals of the zeolite are formed. The temperatures during the hydrothermal crystallization step are typically maintained from about 140° C. to about 200° C., preferably from about 150° C. to about 170° C. and most preferably from about 135° C. to about 165° C. The crystallization period is typically greater than 1 day and preferably from about 3 days to about 7 days.

The hydrothermal crystallization is conducted under pressure and usually in an autoclave so that the reaction mixture is subjected to autogenous pressure. The reaction mixture can be stirred during crystallization.

Once the zeolite crystals have formed, the solid product is separated from the reaction mixture by standard mechanical separation techniques such as filtration. The crystals are water-washed and then dried, e.g., at 90° C. to 150° C. for from 8 to 24 hours, to obtain the as synthesized, SSZ-23 zeolite crystals. The drying step can be performed at atmospheric or subatmospheric pressures.

During the hydrothermal crystallization step, the SSZ-23 crystals can be allowed to nucleate spontaneously from the reaction mixture. The reaction mixture can also be seeded with SSZ-23 crystals both to direct, and accelerate the crystallization, as well as to minimize the formation of undesired aluminosilicate contaminants. If the reaction mixture is seeded with SSZ-23 crystals, the concentration of the organic compound can be greatly reduced or eliminated, but it is preferred to have some organic compound present, e.g., an alcohol.

The synthetic SSZ-23 zeolites can be used as synthesized or can be thermally treated (calcined). Usually, it is desirable to remove the alkali metal cation by ion exchange and replace it with hydrogen, ammonium, or any desired metal ion. The zeolite can be leached with chelating agents, e.g., EDTA or dilute acid solutions, to increase the silica:alumina mole ratio. The zeolite can also be steamed; steaming helps stabilize the crystalline lattice to attack from acids. The zeolite can be used in intimate combination with hydrogenating components, such as tungsten, vanadium, molybdenum, rhenium, nickel, cobalt, chromium, manganese, or a noble metal, such as palladium or platinum, for those applications in which a hydrogenation-dehydrogenation function is desired. Typical replacing cations can include metal cations, e.g., rare earth, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, Fe and Co are particularly preferred.

The hydrogen, ammonium, and metal components can be exchanged into the zeolite. The zeolite can also be impregnated with the metals, or, the metals can be physically intimately admixed with the zeolite using standard methods known to the art. And, the metals can be occluded in the crystal lattice by having the desired metals present as ions in the reaction mixture from which the SSZ-23 zeolite is prepared.

Typical ion exchange techniques involve contacting the synthetic zeolite with a solution containing a salt of the desired replacing cation or cations. Although a wide variety of salts can be employed, chlorides and other halides, nitrates, and sulfates are particularly preferred. Representative ion exchange techniques are disclosed in a wide variety of patents including U.S. Pat. Nos. 3,140,249; 3,140,251; and 3,140,253. Ion exchange can take place either before or after the zeolite is calcined.

Following contact with the salt solution of the desired replacing cation, the zeolite is typically washed with water and dried at temperatures ranging from 65° C. to about 315° C. After washing, the zeolite can be calcined in air or inert gas at temperatures ranging from about 200° C. to 820° C. for periods of time ranging from 1 to 48 hours, or more, to produce a catalytically active product especially useful in hydrocarbon conversion processes.

Regardless of the cations present in the synthesized form of the zeolite, the spatial arrangement of the atoms which form the basic crystal lattice of the zeolite remains essentially unchanged. The exchange of cations has little, if any, effect on the zeolite lattice structures.

The SSZ-23 aluminosilicate can be formed into a wide variety of physical shapes. Generally speaking, the zeolite can be in the form of a powder, a granule, or a molded product, such as extrudate having particle size sufficient to pass through a 2-mesh (Tyler) screen and be retained on a 400-mesh (Tyler) screen. In cases where the catalyst is molded, such as by extrusion with an organic binder, the aluminosilicate can be extruded before drying, or, dried or partially dried and then extruded. The zeolite can be composited with other materials resistant to the temperatures and other conditions employed in organic conversion processes. Such matrix materials include active and inactive materials and synthetic or naturally occurring zeolites as well as inorganic materials such as clays, silica and metal oxides. The latter may occur naturally or may be in the form of gelatinous precipitates, sols, or gels, including mixtures of silica and metal oxides. Use of an active material in conjunction with the synthetic zeolite, i.e., combined with it, tends to improve the conversion and selectivity of the catalyst in certain organic conversion processes. Inactive materials can suitably serve as diluents to control the amount of conversion in a given process so that products can be obtained economically without using other means for controlling the rate of reaction. Frequently, zeolite materials have been incorporated into naturally occurring clays, e.g., bentonite and kaolin. These materials, i.e., clays, oxides, etc., function, in part, as binders for the catalyst. It is desirable to provide a catalyst having good crush strength, because in petroleum refining the catalyst is often subjected to rough handling. This tends to break the catalyst down into powders which cause problems in processing.

Naturally occurring clays which can be composited with the synthetic zeolites of this invention include the montmorillonite and kaolin families, which families include the sub-bentonites and the kaolins commonly known as Dixie, McNamee, Georgia and Florida clays or others in which the main mineral constituent is halloysite, kaolinite, dickite, nacrite, or anauxite. Fibrous clays such as sepiolite and attapulgite can also be used as supports. Such clays can be used in the raw state as originally mined or can be initially subjected to calcination, acid treatment or chemical modification.

In addition to the foregoing materials, the SSZ-23 zeolites can be composited with porous matrix materials and mixtures of matrix materials such as silica, alumina, titania, magnesia, silica:alumina, silica-magnesia, silica-zirconia, silica-thoria, silica-beryllia, silica-titania, titania-zirconia as well as ternary compositions such as silica-alumina-thoria, silica-alumina-zirconia, silica-alumina-magnesia and silica-magnesia-zirconia. The matrix can be in the form of a cogel.

The SSZ-23 zeolites can also be composited with other zeolites such as synthetic and natural faujasites (e.g., X and Y), erionites, and mordenites. They can also be composited with purely synthetic zeolites such as those of the ZSM series. The combination of zeolites can also be composited in a porous inorganic matrix.

SSZ-23 zeolites are useful in hydrocarbon conversion reactions. Hydrocarbon conversion reactions are chemical and catalytic processes in which carbon containing compounds are changed to different carbon containing compounds. Examples of hydrocarbon conversion reactions include catalytic cracking, hydrocracking, and olefin and aromatics formation reactions. The catalysts are useful in other petroleum refining and hydrocarbon conversion reactions such as isomerizing n-paraffins and naphthenes, polymerizing and oligomerizing olefinic or acetylenic compounds such as isobutylene and butene-1, reforming, alkylating, isomerizing polyalkyl substituted aromatics (e.g., ortho xylene), and disproportionating aromatics (e.g., toluene) to provide mixtures of benzene, xylenes and higher methylbenzenes. The SSZ-23 catalysts have high selectivity, and under hydrocarbon conversion conditions can provide a high percentage of desired products relative to total products.

SSZ-23 zeolites can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, and, in general, can be any carbon containing fluid susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

SSZ-23 is especially useful as a catalyst in a process for isomerizing one or more xylene isomers in a $C_8$ aromatic feed to obtain ortho-, meta- and para-xylene in a ratio approaching the equilibrium value. In particular, xylene isomerization is used in conjunction with a separation process to manufacture para-xylene. For example, a portion of the para-xylene in a mixed $C_8$ aromatics stream may be recovered by crystallization and centrifugation. The mother liquor from the crystallizer is then reacted under xylene isomerization conditions to restore ortho-, meta-, and para-xylenes to a near equilibrium ratio. At the same time, part of the ethylbenzene in the mother liquor is converted to xylenes or to products which are easily separated by distillation. The isomerate is blended with fresh feed and the combined stream is distilled to remove heavy and light by-products. The resultant $C_8$ aromatics stream is then sent to the crystallizer to repeat the cycle.

Xylene isomerization catalysts are judged on their ability to produce a near equilibrium mixture of xylenes and convert ethylbenzene with very little net loss of xylenes. The SSZ-23 type zeolites are especially effective in this regard. Accordingly, an additional aspect of the present invention is to provide a hydrocarbon conversion process which comprises contacting a $C_8$ aromatic stream of xylenes, ethylbenzene or mixture thereof, as well as a mixture of ethylbenzenes and other alkyl benzenes under isomerization conditions with a catalyst comprising SSZ-23.

The SSZ-23 may conveniently be used as an aggregate in the form of pellets or extrudates. An inorganic oxide binder such as gamma alumina or silica may be employed to provide attrition resistance.

In the vapor phase, suitable isomerization conditions include a temperature in the range 500°–1100° F., preferably 600°–1050° F., a pressure in the range 0.5–50 atm abs, preferably 1–5 atm abs, and a weight hourly space velocity (WHSV) of 0.1 to 100, preferably 0.5 to 50. Optionally, isomerization in the vapor phase is conducted in the presence of 3.0 to 30.0 moles of hydrogen per mole of alkylbenzene. If hydrogen is used the catalyst should comprise 0.1 to 2.0 wt % of a hydrogenation/dehydrogenation component selected from Group VIII of the Periodic Table, especially platinum or nickel. By Group VIII metal component is meant the metals and their compounds such as oxides and sulfides.

In the liquid phase, suitable isomerization conditions include a temperature in the range 100°–700° F., a pressure in the range 1–200 atm abs, and a WHSV in the range 0.5–50. Optionally, the isomerization feed may contain 10 to 90 wt % of a diluent such as toluene, trimethylbenzenes, naphthenes or paraffins.

SSZ-23 can be used to condense lower aliphatic alcohols having 1 to 8 carbon atoms to a gasoline boiling point hydrocarbon product comprising mixed aliphatic and aromatic hydrocarbon. The condensation reaction proceeds at a temperature of about 500° F. to 1000° F., a pressure of about 0.5 to 1000 psig and a space velocity of about 0.5 to 50 WHSV. The process disclosed in U.S. Pat. No. 3,984,107 more specifically describes the process conditions used in this process, which patent is incorporated totally herein by reference.

The catalyst may be in the hydrogen form or may be base exchanged or impregnated to contain ammonium or a metal cation complement, preferably in the range of from about 0.05 to 5% by weight. The metal cations that may be present include any of the metals of the Groups I through VIII of the Periodic Table. However, in the case of Group IA metals the cation content should in no case be so large as to effectively inactivate the catalyst.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., platinum, include hydrogenation-dehydrogenation reactions, denitrogenation and desulfurization reactions.

SSZ-23 can be used in hydrocarbon conversion reactions with active or inactive supports, with organic or inorganic binders, and with and without added metals. These reactions are well known to the art, as are the reaction conditions.

SSZ-23 can also be used as an adsorbent, as a filler in paper, paint, and toothpastes, and as a water-softening agent in detergents.

The following examples illustrate the preparation of SSZ-23.

EXAMPLES

EXAMPLE 1

Preparation of
N,N,N-Trimethyl-1-adamantanammonium Hydroxide
(Template A)

Ten (10) grams of 1-adamantanamine (Aldrich) was dissolved in a mixture of 29 gms tributylamine and 60 mls dimethylformamide. The mixture was chilled in an ice bath.

28.4 Grams of methyl iodide were added dropwise to the chilled solution with continuous stirring. After several hours crystals appear. The reaction was continued overnight and allowed to come to room temperature. The crystals were filtered and washed with tetrahydrofuran and then diethyl ether before vacuum drying.

Additional product was obtained by adding enough diethyl ether to the reaction filtrate to produce two phases and then with vigorous stirring acetone was added until the solution just became one phase. Continued stirring produced crystallization at which time the solution can be chilled to induce further crystallization. The product has a melting point near 300° C. (decomp.) and the elemental analyses and NMR are consistent with the known structure. The vacuum-dried iodide salt was then ion-exchanged with ion-exchange resin AG 1×8 (in molar excess) to the hydroxide form. The exchange was performed over a column or more preferably by overnight stirring of the resin beads and the iodide salt in an aqueous solution designed to give about a 0.5 molar solution of the organic hydroxide. This produces Template A.

EXAMPLE 2

Preparation of N,N,N-Trimethyl-2-adamantanammonium Hydroxide (Template B)

Five grams of 2-adamantanone (Aldrich Chemical Co.) was mixed with 2.63 gms of formic acid (88%) and 4.5 gms of dimethyl formamide. The mixture was then heated in a pressure vessel for 16 hours at 190° C. Care should be taken to anticipate the increase in pressure the reaction experiences due to $CO_2$ evolution. The reaction was conveniently carried out in a Parr 4748 reactor with teflon liner. The workup consists of extracting N,N dimethyl-2-adamantamine from a basic (pH=12) aqueous solution with diethyl ether. The various extracts were dried with $Na_2SO_4$ the solvent removed and the product taken up in ethyl acetate. An excess of methyl iodide was added to a cooled solution which was then stirred at room temperature for several days. The crystals were collected and washed with diethyl ether to give N,N,N trimethyl-2-adamantammonium iodide. The product was checked by microanalysis for C, H, and N. The conversion to the hydroxide form was carried out analogously to Template A above.

EXAMPLE 3

0.12 Grams of $Al_2(SO_4)_3 \cdot 18H_2O$ were dissolved in a solution of 0.26 gms KOH (solid) in 16 ml of a 0.26 molar template hydroxide prepared according to Example 1. 1.21 Grams of Cabosil M5 was slowly added with stirring and the contents on the ensuing thin gel were placed in the Teflon liner of Parr 4745 reactor. The reactor was placed on a rotating spit inside a Blue M oven and rotated at 30 RPM while heating the reaction to 175° C. for 7 days. Upon cooling, the sample and filtration, a fine white solid, was collected. By X-ray diffraction, the product was zeolite SSZ-23 with a trace of zeolite SSZ-13 as impurity. Using the BET method for nitrogen absorption and desorption, the surface area of zeolite after calcination to 1100° F., ion-exchanged with $NH_4NO_3$ (4 times) and recalcining at 1000° F. (to yield the hydrogen form), was approximately 400 $cm^2$/gm with a micropore volume of about 0.16 cc/gm. In the as-made form, the zeolite SSZ-23 shows $C/N^+$ ratios close to 13, the ratio in the template, and the organic content accounts for about 15% of the product mass indicating substantial pore filling by the template during synthesis.

EXAMPLE 4

0.12 Grams of $Al_2(SO_4)_3 \cdot 18H_2O$, 0.26 gms of KOH (solid) and 4 ml of a 1 molar solution of the template hydroxide of Example 1 were dissolved in 12 mls $H_2O$. 1.20 Grams of Cabosil M5 were blended into the solution and the mixture was heated and worked up as in Example 3. The product by X-ray diffraction was zeolite SSZ-23 with quartz as an impurity.

EXAMPLE 5

0.087 Grams of KOH (solid), 0.06 gms of $Al_2(SO_4)_3 \cdot 18H_2O$ and 5 grams of a 0.74 molar solution of the template hydroxide of Example 1 were dissolved in 4 ml of $H_2O$ containing 4 micromoles of methylene Blue Dye. 0.60 Grams of Cabosil M5 was stirred in. The reaction was sealed in the same Parr reactor as Example 3 and heated for 7 days at 30 RPM, but with the reaction temperature reduced to 160° C. The cooled reaction was opened and the fine white solids are recovered by filtration. After working with copious quantities of distilled water, the product was air-dried overnight. After drying at 100° C. analysis by the X-ray diffraction pattern, as demonstrated in Table 3 below, shows the material to be pure SSZ-23. The ratio of reactants in this run were:

$Si:O_2/Al_2O_3 = 100$
$KOH/SiO_2 = 0.13$
TEMPLATE $OH^-/SiO_2 = 0.37$
$H_2O/SiO_2 = 44$
net $OH^-/SiO_2 = 0.45$ The most frequently encountered impurity in the preparation of zeolite SSZ-23 can be zeolite SSZ-13. To minimize the formation of the latter zeolite, I have found it advantageous to (a) exclude $Na^+$ ion from the preparation and (b) to use methylene Blue at a level of methylene Blue/$Al_2O_3 = 4.4 \times 10^{-2}$. The methylene Blue is known to inhibit the nucleation of certain zeolite phases (Whittam et al British Patent No. 1,450,411) and because zeolite SSZ-13 is a high silica chabazite structure, this particular dye seems to be effective in preventing its crystallization in zeolite SSZ-23 syntheses.

TABLE 3

| $2\theta$ | d/n | $I/I_o$ |
| --- | --- | --- |
| 8.18 | 10.81 | 100 |
| 8.60 | 10.28 | 27 |
| 9.52 | 9.29 | 33 |
| 10.57 | 8.37 | 43 |
| 14.53 | 6.10 | 30 |
| 15.57 | 5.69 | 27 |
| 17.63 | 5.03 | 37 |
| 18.07 | 4.91 | 43 |
| 18.56 | 4.78 | 80 |
| 19.00 | 4.67 | 13 |
| 19.67 | 4.51 | 60 |
| 20.08 | 4.42 | 60 |
| 20.33 | 4.37 | 20 |
| 20.67 | 4.30 | 43 |
| 21.13 | 4.205 | 10 |
| 21.55 | 4.123 | 90 |
| 22.18 | 4.008 | 43 |
| 22.47 | 3.957 | 33 |
| 22.75 | 3.909 | 57 |
| 23.35 | 3.810 | 33 |
| 23.72 | 3.751 | 20 |
| 24.00 | 3.708 | 10 |
| 24.49 | 3.635 | 27 |
| 24.91 | 3.574 | 43 |
| 25.54 | 3.488 | 10 |
| 26.62 | 3.349 | 27 |
| 26.91 | 3.313 | 23 |
| 27.37 | 3.258 | 20 |
| 27.86 | 3.202 | 20 |
| 28.31 | 3.152 | 13 |
| 28.60 | 3.121 | 17 |
| 29.17 | 3.061 | 10 |
| 29.54 | 3.024 | 17 |

TABLE 3-continued

| 2θ | d/n | I/I$_o$ |
|---|---|---|
| 30.05 | 2.974 | 10 |
| 30.63 | 2.919 | 23 |

EXAMPLE 6

The same reactants were used as in Example 5 but changes were made to yield the following ratios of reactants:

SiO$_2$/Al$_2$O$_3$ = 120
KOH/SiO$_2$ = 0.22
Template OH$^-$/SiO$_2$ = 0.22
H$_2$O/SiO$_2$ = 44
OH$^-$/SiO$_2$ = 0.38
Methylene Blue/Al$_2$O$_3$ = 1×10$^{-3}$.

The reaction mixture was heated as in Example 5 and worked up in an analogous fashion. The crystalline product was zeolite SSZ-23 with a tridymite-like silica impurity. In general, zeolite SSZ-23 crystallizes in discs of about 1–6 μ length.

EXAMPLE 7

In this example the KOH of Example 5 was replaced by 0.047 gms of NaOH. The remaining reagents of Example 5 were the same. The reaction was run and worked up as in Example 5 except the run time was 6 days. The zeolite product was again SSZ-23.

EXAMPLE 8

Another run was set up and run as in Example 5. Here, the alkali cation was rubidium and it was supplied by using 0.17 gms of a 50% solution of rubidium hydroxide (Alfa Inorganics). The crystalline product was SSZ-23.

EXAMPLE 9

This run uses 0.25 gms of 50% CsOH as the alkali source. Using the same run conditions as Example 5 the product was SSZ-23.

EXAMPLE 10

In this reaction the starting SiO$_2$/Al$_2$O$_3$ ratio was 50, so the resulting ratio in the zeolite product will be lower than in Examples 5 to 9 above (which had initial SiO$_2$/Al$_2$O$_3$ values of 120). Once again the reaction was carried out in a Parr 4745 reactor. 4.15 Grams of Template B of Example 2 (0.72M) was mixed with 5 mls water, 0.59 gms of 50% rubidium hydroxide and 2.36 gms of Ludox AS-30 colloidal silica. After stirring the reagents with a stir bar as above, 0.78 gms of Nalco 1SJ612 colloidal silica with alumina dispersed on it was blended in. The reactor was sealed, loaded onto the spit and heated at 175° C. for ten days while rotating at 30 RPM with the stir bar still in the reactor. The resulting product after the appropriate workup was SSZ-23.

EXAMPLE 11

This example illustrates the synthesis of SSZ-23 from a mixture with SiO$_2$/Al$_2$O$_3$ = 200. Using the same equipment including the pea shape stirrer as in the preceding examples, the following reagents were mixed: 5.6 ml of Template A (0.70M), 0.065 gms of KOH(s), and 0.06 gms of Al$_2$(SO$_4$)$_3$· 18 H$_2$O was dissolved in 10.2 ml H$_2$O. Then 1.20 gms of Cabosil M5 were added. The reaction was run for 6 days at 160° C. with 30 RPM agitation. The product was crystalline SSZ-23.

EXAMPLE 12

SSZ-23 can be formed in an essentially aluminum-free system. 54.4 Grams of Template A (0.72M), and 0.65 gms of KOH(s) were dissolved in 110 ml H$_2$O. 12.71 Grams of Cabosil M5 were added and stirred. The reaction mixture was loaded into a 600 cc Parr stirred reactor and heated at 160° C. for 6 days with 100 RPM stirring. The product upon workup was crystalline SSZ-23. The X-ray diffraction pattern of this product is given in Table 4 below.

TABLE 4

| 2θ | d/n | I/I$_o$ |
|---|---|---|
| 8.12 | 10.89 | 100 |
| 8.56 | 10.33 | 60 |
| 9.47 | 9.34 | 75 |
| 10.53 | 8.40 | 40 |
| 14.48 | 6.12 | 25 |
| 15.56 | 5.70 | 25 |
| 17.58 | 5.04 | 50 |
| 18.02 | 4.92 | 30 |
| 18.51 | 4.79 | 80 |
| 18.93 | 4.69 | 25 |
| 19.62 | 4.52 | 100 |
| 20.04 | 4.43 | 100 |
| 20.32 | 4.37 | 15 |
| 20.63 | 4.305 | 30 |
| 21.04 | 4.222 | 10 |
| 21.50 | 4.133 | 100 |
| 22.13 | 4.017 | 60 |
| 22.43 | 3.964 | 40 |
| 22.68 | 3.920 | 80 |
| 23.31 | 3.816 | 25 |
| 23.67 | 3.759 | 20 |
| 23.93 | 3.719 | 10 |
| 24.47 | 3.638 | 20 |
| 24.83 | 3.586 | 45 |
| 25.50 | 3.493 | 10 |
| 26.60 | 3.351 | 25 |
| 26.86 | 3.319 | 20 |
| 27.33 | 3.263 | 25 |
| 27.83 | 3.206 | 15 |
| 28.29 | 3.155 | 10 |
| 28.55 | 3.126 | 25 |
| 29.15 | 3.063 | 10 |
| 29.48 | 3.030 | 15 |
| 30.00 | 2.979 | 10 |
| 30.55 | 2.926 | 35 |

EXAMPLE 13

Six grams of a 0.65M solution of Template B were dissolved in 10 ml H$_2$O along with 0.06 grams of Al$_2$(SO$_4$)$_3$· 18 H$_2$O and 0.11 gms of KOH(s). 1.20 Grams of Cabosil M5 are added and the reaction was run as in Example 11, however, the product was worked up after 15 days with 30 RPM stirring. The product was once again SSZ-23.

EXAMPLE 14

A. The crystalline products of Examples 5, 10 and 12 were subjected to calcination as follows. The samples were heated in a muffle furnace from room temperature up to 540° C. at a steadily increasing rate over a 7-hour period. The samples were maintained at 540° C. for four more hours and then taken up to 600° C. for an additional four hours. A 50/50 mixture of air and nitrogen was passed over the zeolites at a rate of 20 standard cubic feet per minute during heating.

The calcined product of Examples 12 and 5 had representative X-ray diffraction patterns as indicated in Tables 5 and 6, respectively.

TABLE 5

| 2θ | d/n | I/I$_o$ |
|---|---|---|
| 8.16 | 10.84 | 80 |
| 8.50 | 10.40 | 32 |
| 9.43 | 9.38 | 100 |
| 10.56 | 8.38 | 38 |
| 13.28 | 6.67 | 7 |
| 13.85 | 6.39 | 5 |
| 17.78 | 4.99 | 7 |
| 18.59 | 4.77 | 19 |
| 19.59 | 4.53 | 16 |
| 20.03 | 4.433 | 9 |
| 21.58 | 4.118 | 14 |
| 22.12 | 4.019 | 8 |
| 22.55 | 3.943 | 11 |
| 24.60 | 3.619 | 6 |
| 24.92 | 3.573 | 8 |
| 26.65 | 3.345 | 8 |
| 28.48 | 3.134 | 8 |

TABLE 6

| 2θ | d/n | I/I$_o$ |
|---|---|---|
| 7.94 | 11.41 | 22 |
| 8.07 | 10.96 | 44 |
| 8.17 | 10.82 | 100 |
| 8.50 | 10.40 | 16 |
| 9.47 | 9.34 | 76 |
| 10.56 | 8.38 | 49 |
| 13.27 | 6.67 | 9 |
| 13.88 | 6.38 | 7 |
| 17.78 | 4.99 | 8 |
| 18.57 | 4.78 | 21 |
| 19.66 | 4.515 | 12 |
| 20.08 | 4.422 | 8 |
| 21.58 | 4.118 | 15 |
| 22.12 | 4.019 | 7 |
| 22.56 | 3.941 | 11 |
| 24.60 | 3.619 | 7 |
| 24.89 | 3.577 | 8 |
| 26.60 | 3.351 | 7 |
| 28.60 | 3.132 | 5 |

B. Ion-exchange of the calcined materials from A. above of Examples 5, 10 and 12 was carried out using NH$_4$NO$_3$ to convert the zeolites from their K form to NH$_4$ and then eventually H form. Typically the same mass of NH$_4$NO$_3$ as zeolite was slurried into H$_2$O at ratio of 50/1 H$_2$O to zeolite. The exchange solution was heated at 100° C. for two hours and then filtered. This process was repeated four times. Finally, after the last exchange the zeolite was washed several times with H$_2$O and dried. A repeat calcination as in A. above was carried out but without the final treatment at 600° C. This produces the H form of the zeolites.

EXAMPLE 15

Constraint Index Determination 0.25 Grams of the hydrogen form of the zeolite of Examples 5, 10 and 12 (after treatment according to Example 14, parts A. and B.) were packed separately into a ⅜″ stainless steel tube with alundum on both sides of the zeolite bed. A Lindburg furnace was used to heat the reactor tube. Helium was introduced into the reactor tube at 10 cc/min. and atmospheric pressure. The reactor was taken to 250° F. for 40 min. and then raised to 800° F. Once temperature equilibration was achieved a 50/50, w/w feed of n-hexane and 3-methylpentane was introduced into the reactor at a rate of 0.62 cc/hr. Feed delivery was made via syringe pump. Direct sampling onto a gas chromatograph began after 10 minutes of feed introduction. Constraint Index values were calculated from gas chromatographic data using methods known in the art.

| Example No. | C.I. | Conversion at 10 min. | Temp. °F. |
|---|---|---|---|
| 5 | 4 | 9% | 800 |
| 12 | — | 0% | 800 |
| 10 | 2 | 16% | 800 |

EXAMPLE 16

The hydrogen form of the SSZ-23 zeolite was tested as catalyst for xylene isomerization. A portion of the HSSZ-23 powder was pelleted, crushed and sieved to obtain 20-40 mesh granules, which were then calcined for four hours at 1000° F. One gram of the calcined material was charged to a 3/16-inch I.D. tubular microreactor heated by an electric furnace. The catalyst bed was heated to 850° F. in flowing helium. The helium was then replaced with a mixed xylene feed. The feed composition and reactor effluent were analyzed by gas chromatography. The test results are shown in Table 7. The HSSZ-23 catalyst produced a near equilibrium mixture of xylene isomers with excellent ethylbenzene conversion and very little xylene loss.

TABLE 7

Xylene Isomerization Over HSSZ-23

| Hours on Stream | 2-4 | 8-23 |
|---|---|---|
| Temperature, °F. | 850 | 825 |
| WHSV | 5 | 5 |
| Pressure, psig | 24 | 26 |

| Composition, Wt % | Feed | Products | |
|---|---|---|---|
| non-aromatics | 0.44 | 1.60 | 1.40 |
| benzene | 0.00 | 3.95 | 2.70 |
| toluene | 1.34 | 2.65 | 2.06 |
| ethylbenzene | 9.76 | 4.32 | 6.04 |
| p-xylene | 9.61 | 19.69 | 19.50 |
| m-xylene | 53.99 | 44.11 | 44.79 |
| o-xylene | 23.10 | 20.45 | 20.68 |
| heavy aromatics | 1.77 | 3.25 | 2.84 |
| Percent EB conversion | | 55.7 | 38.1 |
| Percent Xylene Loss | | 2.5 | 1.7 |
| p-xyl & approach to equil. | | 100.2 | 96.4 |

EXAMPLE 17

The same catalyst as used in Example 16 above was also tested for methanol conversion. 0.5 Grams of catalyst was packed in a ⅜-inch stainless steel reactor tube which was heated to 100° F. in a furnace. The reactor was brought back down to 800° F. in a stream of dry helium. Methanol was introduced into the reactor at a rate of 1.3 cc/hr and a helium flow rate of 20 cc/hr. Initial conversion was 100% and the hydrocarbon products are given in Table 8.

TABLE 8

Methanol Conversion over HSSZ-23 at 10 Minutes on Stream

| Product | Weight Percent |
|---|---|
| Methane | 3.4 |
| Ethylene | 19.9 |
| Ethane | 2.0 |
| Propylene | 19.4 |
| Propane | 20.1 |
| C$_4$ Olefins | 10.4 |
| C$_4$ Paraffins | 9.7 |
| C$_5$ | 5.4 |
| Benzene | 1.3 |
| Toluene | 4.0 |
| P-xylene | 4.5 |

What is claimed is:

1. A process for the conversion of lower aliphatic alcohols having 1 to 8 carbon atoms to form gasoline boiling range hydrocarbons which comprises contacting the alcohols under converting conditions with a zeolite having a mole ratio of an oxide selected from silicon oxide, germanium oxide and mixtures thereof to an oxide selected from aluminum oxide, gallium oxide, iron oxide, boron oxide and mixtures thereof greater than about 50:1, and having the x-ray diffraction lines of Table 1.

2. The process of claim 1 wherein the alcohol is methanol.

3. The process of claim 1 is carried out in contact with HSSZ-23.

* * * * *